United States Patent [19]

Roerink

[11] Patent Number: 4,650,677

[45] Date of Patent: Mar. 17, 1987

[54] METHOD OF PREPARING ADJUVANTED LIVE ATTENUATED VACCINES AND ADJUVANTED LIVE ATTENUATED VACCINES THUS OBTAINED

[75] Inventor: Jan H. G. Roerink, Weesp, Netherlands

[73] Assignee: Duphar International Research B.V., Weesp, Netherlands

[21] Appl. No.: 616,144

[22] Filed: Jun. 1, 1984

[30] Foreign Application Priority Data

Jun. 6, 1983 [NL] Netherlands ............... 8301996

[51] Int. Cl.$^4$ ............................................. A61K 39/12
[52] U.S. Cl. ......................................... 424/89; 424/88
[58] Field of Search ................................. 424/89, 88

[56] References Cited

U.S. PATENT DOCUMENTS

| | | | |
|---|---|---|---|
| 3,083,142 | 3/1963 | Howell et al. | 424/89 |
| 3,149,036 | 9/1964 | Woodhour et al. | 424/89 |
| 3,376,199 | 4/1968 | Coles et al. | 424/89 |
| 3,378,443 | 4/1968 | Cooper et al. | 424/89 |
| 3,399,263 | 8/1968 | Strazdins et al. | 424/89 |
| 3,435,112 | 3/1969 | Kuhns et al. | 424/89 |
| 3,492,399 | 1/1970 | Prigal | 424/89 |
| 3,594,471 | 7/1971 | Hertzberger et al. | 424/89 |
| 3,678,149 | 7/1972 | Prigal | 424/89 |
| 3,790,665 | 2/1974 | Glass et al. | 424/89 |
| 3,919,411 | 11/1975 | Glass et al. | 424/89 |
| 3,983,228 | 9/1976 | Woodhour et al. | 424/89 |
| 4,069,313 | 1/1978 | Woodhour et al. | 424/89 |
| 4,073,743 | 2/1978 | Midler et al. | 424/89 |
| 4,125,603 | 11/1978 | Audibert et al. | 424/89 |

FOREIGN PATENT DOCUMENTS 0129923  1/1985  European Pat. Off. ............. 424/89

OTHER PUBLICATIONS

Van Oirschot et al., Am. J. Vet. Res. 45(10):2099–2103, Oct. 1984, Intranasal Vaccination of Pigs Against Pseudorabies: Absence of Vaccinal Virus Latency and Failure to Prevent Latency of Viruent Virus.

Stott et al., Hyg. Camb. 93-251–264 (1984), A Comparison of Three Vaccines Against Respiratory Syncytial Virus in Calves.

"Studies on Immunisation of Pigs with the Bartha Strain of Aujeszky's Disease Virus", Research in Veterinary Science, 1975, vol. 19, pp. 17–22.

*Primary Examiner*—Shep K. Rose
*Attorney, Agent, or Firm*—Stevens, Davis, Miller & Mosher

[57] ABSTRACT

A live attenuated adjuvanted Aujeszky vaccine is prepared by dissolving freeze-dried Aujeszky virus Bartha strain in an oil-in-water emulsion. The vaccine is used to vaccinate pigs against Aujeszky disease.

3 Claims, No Drawings

METHOD OF PREPARING ADJUVANTED LIVE ATTENUATED VACCINES AND ADJUVANTED LIVE ATTENUATED VACCINES THUS OBTAINED

The invention relates to a method of preparing live vaccines and to the live vaccines thus obtained.

It is known that live attenuated viruses generally are less immunogenic than the original virulent virus from which they are derived. The attenuation is meant to remove the virulence or at any rate to reduce it so strongly that the virus thus attenuated can safely be administered. However, this attenuation usually also results in a reduced immunogenic activity.

Live virus vaccines are as a rule freeze-dried in order to stabilise the infectiosity, as a result of which such a live vaccine is longer stable. A live vaccine is dissolved prior to administration, for example, in a physiological saline solution or sometimes in an inactivated vaccine. Such an inactivated vaccine is nearly always an Al-(OH)$_3$ adsorbed vaccine. Only for practical reasons is such a live virus vaccine combined with an inactivated vaccine: as a matter of fact both can now be administered simultaneously. As a rule, such a combination does not result in a better potency of the live component.

It has so far been taken for granted that a higher immune response could be achieved with live vaccines, for example, by increasing the virus content, or by using a more immunogenic strain.

It has surprisingly been found that the use of an oil-in-water (o/w) emulsion as the "solvent" for live vaccines has a positive effect on the serological and immune response in the vaccinated animals. In this oil-in-water emulsion, the aqueous phase is present on the outside and the freezedried live vaccine can easily be dissolved in it.

A further aspect of the invention is that it has been found that by using the o/w-emulsion as solvent for live vaccines a very high serological response is obtained in young animals still having maternal immunity. This surprising effect may be caused by a protective action of the o/w-emulsion on the live virus against neutralisation by the antibodies which are present in the animal.

A still further embodiment of the invention is that instead of taking up the live vaccine(s) in the o/w-emulsion as such, said live vaccine may be taken up in an inactivated vaccine or combination of vaccines containing the o/w-emulsion.

The oily phase of the emulsion to be used according to the invention is a mineral oil, for example Marcol® or Drakeol®. The quantity of oil in the emulsion is usually between 15 and 50% by volume, preferably 20–30% by volume.

The emulsion to be used can be obtained in the conventional manner while using emulsifying agents suitable for the preparation of o/w-emulsions.

The invention will now be described in greater detail with reference to a few experiments with a live attenuated Aujeszky vaccine based on the Bartha strain, with a live attenuated Infectious Bovine Rhinotracheitisvirus (IBRV) vaccine, and with a live attenuated Respiratory Syncytial-Virus vaccine (RSV).

It is known that the Bartha strain is not very immunologically active, in particular in piglets which still have maternally obtained antibodies. Nor did an increased virus content of this vaccine prove capable of inducing a sufficiently high serum titer.

By using an oil-in-water emulsion according to the invention, a surprisingly higher serological response was obtained with the same virus material.

EXAMPLE I

Since an important field of application of live Aujeszky vaccines is the vaccination of young fattening pigs which still have a maternal antibody titer with respect to Aujeszky's disease, a comparative serological experiment has been set up using the said animals. The results hereof are recorded in Table A.

TABLE A

Average serum neutralisation (SN)-titers prior to and after vaccination with the Bartha vaccine, dissolved in physiological saline or in a 25% o/w emulsion.

| Type of vaccine | Group | age on vaccination | Number of animals | 2 weeks before vaccin. | Day of vac. | Number of weeks after vaccination 2 | 4 | 6 | 8 | 10 |
|---|---|---|---|---|---|---|---|---|---|---|
| Physiol. | I | 18 w | 6 | 3.8 | 1.6 | 7.3 | 10.8 | — | — | — |
| saline | II | 16 w | 6 | 9.1 | 1.6 | 11.5 | 5.8 | — | — | — |
| | III | 14 w | 8 | 4.3 | 1.3 | 5.3 | 6.1 | 4.5 | — | 6.8 |
| o/w | IV | 14 w | 8 | 4.5 | 2.3 | 16.2 | 18.9 | 22.9 | — | 47.3 |
| emuls. | V | 11 w | 8 | 23.8 | 6.6 | 11.7 | 13.4 | 19.4 | 29.4 | — |

— = not carried out

Blood samples for the determination of the antibody titer were taken 2 weeks before vaccination, on the day of vaccination and on several weeks after vaccination as recorded in Table A.

From the SN-titers stated in Table A the following appears:

The Bartha vaccine in physiological saline is not capable of producing a satisfactory serological response, even in animals which have only a very low maternal immunity (1.3–1.6). At the moment of vaccination, these animals were 14–18 weeks of age.

The Bartha vaccine in o/w emulsion on the contrary gives good serum titers upon administration to piglets having a maternal immunity of 2.3 or 6.6. Upon vaccination these animals were 11 to 14 weeks of age.

EXAMPLE II

Another field of application is the vaccination of young guilts and sows. The usefulness in this case is determined substantially by the titer height reached in the mother animal, because only then can a sufficiently long containing maternal immunity with respect to Aujeszky's disease in the offspring be ensured.

Starting from maternally immune young guilts, a comparison has been made between the Bartha vaccine dissolved in physiological saline solution and the same vaccine dissolved in 25% o/w emulsion. Both vaccines were administered twice.

TABLE B

Average SN-titers before and after 1st and 2nd vaccination with the Bartha vaccine dissolved in a 25% o/w emulsion and the same vaccine dissolved in physiological saline solution.

| Type of vaccine | Group | Numb. of animals | Age on 1st vac. (weeks) | SN-titer before 1st vaccin. | Number of weeks after 1st vaccination |  |  |  |  |
|---|---|---|---|---|---|---|---|---|---|
|  |  |  |  |  | 2 | 4 | 8 | 10 | 12 |
| Physiol. saline | VI | 6 | 12 | 6.3 | 6.3 | 6.3* | 63 | — | — |
| o/w emulsion | VII | 4 | 11 | 5.8 | 11.6 | 20.3 | 54* | 7080 | 3928 |
|  | VIII | 4 | 11 | 4.9 | 10.3 | 22.5 | 23* | 4623 | 3012 |

— = not carried out
* = moment of 2nd vaccination

From Table B it again appears that the Bartha vaccine in o/w formulation in the first vaccination breaks through the maternal immunity considerably better and that the same vaccine dissolved in physiological saline solution does not produce any serological response in these maternally immune animals after one vaccination. After the second vaccination there also is a clear difference between the two formulations: only a 10-fold rise in titer is reached with the Bartha vaccine in physiological saline solution; a 130 to 200-fold rise was reached with the Bartha vaccine in o/w emulsion.

EXAMPLE III

In this example, a combined Aujeszky-influenza vaccine has been used. The influenza vaccine for pigs is an inactivated vaccine based on a o/w emulsion. The freeze-dried Barth vaccine is dissolved in it immediately before use. For this experiment piglets were used which have no maternal antibodies any longer with respect to Aujeszky's disease, so as to be better able to study a possible negative influence of the influenza component on the Bartha vaccine. The quantity of influenza virus per dose was varied and is expressed as "high", "medium" and "low".

TABLE C

Average Aujeszky SN-titers after 1 or 2 vaccinations with the Aujeszky-influenza vaccine on o/w basis.

| Influenza dose | Number of vaccinations | Number of animals | SN-titer 8 wks after 1st vaccin. | SN-titer 2 wks after 2nd vaccin. |
|---|---|---|---|---|
| "high" | 2x | 4 | 195* | 3016 |
|  | 1x | 3 | 159 | 132 |
| "medium" | 2x | 4 | 116* | 3887 |
|  | 1x | 3 | 112 | 58 |
| "low" | 2x | 4 | 107* | 3887 |
|  | 1x | 3 | 113 | 103 |

*the second vaccination was administered to these animals 8 weeks after the first vaccination It will be clear from Table C that the presence of inactivated influenza virus in the o/w emulsion has no detrimental effect on the results of the live Aujeszky component. The serological response both after 1 and after 2 vaccinations is extremely good.

In various experiments the body temperature of the animals was measured from 1 day before up to and including 3 days after vaccination. At no instant whatsoever after vaccination was an increased temperature observed in the animals vaccinated with the o/w formulation. No local vaccination reactions were found either. The live vaccine in an o/w formulation therefore is to be considered as being safe.

EXAMPLE IV

The effect of the o/w-emulsion of the invention was also examined with live attenuated infectious bovine rhinotracheitis-virus (IBRV) by immunizing cows with the usual amount of vaccine-virus either dissolved in a 25% o/w-emulsion or in a physiological saline solution. The serological responses are indicated in Table D:

TABLE D

Average SN-titers before and after 1 and 2 vaccinations with IBRV-vaccine in 25% o/w or physiological saline.

| Type of vaccine | Number of animals | Number of vaccin. | SN-titer before 1st vaccin. | 3 wks after 1st vaccination | 6 wks after 1st resp. 3 wks after 2nd vac. |
|---|---|---|---|---|---|
| physiol. saline | 4 | 1 | 0 | 1.4 (1)* | 1.6 (1) |
|  | 4 | 2 | 0 | 1.3 (2) | 3.2 (3) |
| o/w-emul. | 4 | 1 | 0 | 3.8 (4) | 3.8 (4) |
|  | 4 | 2 | 0 | 2.9 (4) | 8.5 (4) |
| not vacc. | 4 | 0 | 0 | 0 | 0 |

*The numbers in parentheses indicate the number of cows having a positive SN-titer after vaccination.

The following can be concluded from the SN-titers as indicated in Table D:
1. 100% of the animals vaccinated with the vaccine containing o/w-emulsion according to the invention gives a serological response, whereas only 50% of the animals of the physiological saline group gives a positive response.
2. The SN-titers after vaccination in the o/w-group are 2-3 times as high as in the other group.

EXAMPLE V

In this example the influence of the o/w-emulsion according to the invention on the serological response of live vaccine was examined by vaccinating cows with a live attenuated respiratory syncytial virus-(RSV) vaccine, either in 25% o/w-emulsion or in a physiological saline solution.

The serological responses after vaccination with both types of vaccine are indicated in Table E. With both types of vaccine equal amounts of virus were administered to the cows.

TABLE E

Average indirect immunofluorescence (i.I.F)-RSV-titers after vaccination with RSV-vaccine dissolved in physiological saline solution or in a 25% o/w-emulsion.

| Type of vaccine | Number of animals | i-IF-titer |  |
|---|---|---|---|
|  |  | before vaccination | 3 wks after vacc. |
| physiol. saline | 8 | 380 | 269 |
| o/w-emuls. | 8 | 453 | 3044 |

TABLE E-continued

Average indirect immunofluorescence (i.l.F)-RSV-titers after vaccination with RSV-vaccine dissolved in physiological saline solution or in a 25% o/w-emulsion.

| Type of vaccine | Number of animals | i-IF-titer | |
|---|---|---|---|
| | | before vaccination | 3 wks after vacc. |
| not vacc. | 3 | 172 | 50 |

It appears from the results of Table E that:

Animals vaccinated with RSV-vaccine in a o/w-emulsion show a very high titer, even when a considerable titer is present before vaccination (due to maternal immunity). However, the vaccine dissolved in physiological saline solution causes no increase of the titer in animals with maternal immunity.

I claim:

1. A live attenuated adjuvanted Aujeszky vaccine consisting of Aujeszky virus Bartha strain dissolved in an oil-in-water emulsion containing between 15 and 50% by volume of oil.

2. A live attenuated adjuvanted Aujeszky vaccine consisting of freeze dried Aujeszky virus Bartha strain dissolved in an oil-in-water emulsion containing between 15 and 50% by volume of oil.

3. A method of vaccinating pigs against Aujeszky disease which comprises innoculating pigs with a live attenuated Aujeszky vaccine, said vaccine consisting of Aujeszky virus Bartha strain dissolved in an oil-in-water emulsion containing between 15 and 50% by volume of oil.

* * * * *